US009481892B2

(12) United States Patent
Schumann et al.

(10) Patent No.: US 9,481,892 B2
(45) Date of Patent: Nov. 1, 2016

(54) CONTROLLED ACTIVATION OF NON-LTR RETROTRANSPOSONS IN MAMMALS

(75) Inventors: Gerald Schumann, Dreieich (DE); Liliana Elisabeth Layer, Maxdorf (DE)

(73) Assignee: Liliana Layer, Neustadt Haardt (DE)

( * ) Notice: Subject to any disclaimer, the term of this patent is extended or adjusted under 35 U.S.C. 154(b) by 475 days.

(21) Appl. No.: 12/740,943

(22) PCT Filed: Oct. 30, 2008

(86) PCT No.: PCT/EP2008/009179
§ 371 (c)(1),
(2), (4) Date: Oct. 11, 2010

(87) PCT Pub. No.: WO2009/056321
PCT Pub. Date: May 7, 2009

(65) Prior Publication Data
US 2011/0045591 A1    Feb. 24, 2011

(30) Foreign Application Priority Data
Oct. 31, 2007    (EP) .................................. 070213311

(51) Int. Cl.
| | |
|---|---|
| C12N 15/64 | (2006.01) |
| C12N 1/20 | (2006.01) |
| C12N 15/00 | (2006.01) |
| A61K 48/00 | (2006.01) |
| C12N 15/85 | (2006.01) |
| C12N 15/90 | (2006.01) |

(52) U.S. Cl.
CPC ........... *C12N 15/85* (2013.01); *C12N 15/8509* (2013.01); *C12N 15/90* (2013.01); *C12N 2800/24* (2013.01); *C12N 2800/90* (2013.01); *C12N 2830/003* (2013.01)

(58) Field of Classification Search
None
See application file for complete search history.

(56) References Cited

U.S. PATENT DOCUMENTS

2003/0121063 A1    6/2003    Kazazian et al.
2006/0183226 A1    8/2006    Fujiwara et al.

FOREIGN PATENT DOCUMENTS

WO    88/03169 A1    5/1988

OTHER PUBLICATIONS

Zhang, et al. "PowerBLAST: A New Network Blast Application for Interactive or Automated Sequence Analysis and Annotation," Genome Res. 7:649-656 (1997).
International Search Report, PCT/EP2008/009179, Jan. 16, 2009, 4 pages.
Altschul, et al., "Basic Local Alignment Search Tool," J. Mol. Biol. 215:403-410 (1990).
Altschul, et al., "Gapped BLAST and PSI-BLAST: A New Generation of Protein Database Ssearch Programs," Nucleic Acids Res. 25(17):3389-3402 (1997).
An, et al., "Active Retrotransposition by a Synthetic L1 Element in Mice," PNAS 103(49):18662-18667 (2006).
Babushok, et al., "Progress in Understanding the Biology of the Human Mutagin LINE -1," Human Mutation, 28 (6):527-539 (2007).
Barry, et al., "Stability of Minocycline, Doxycycline, and Tetracycline Stored in Agar Plates and Microdilution Trays," Curr. Microbiol., 1:33-36 (1978).
Belancio, et al., "Mammalian Non-LTR Retrotransposons: For Better or Worse, in Sickness and in Health," Genome Res. 18:343-358 (2008).
Brouha, et al., "Evidence Consistent With Human L1 Retrotransposition in Maternal Meiosis I," Am. J. Hum. Genet. 71:327-336 (2002).
Brouha, et al., "Hot L1 s Account for the Bulk of Retrotransposition in the Human Population," PNAS 100 (9):5280-5285 (2003).
Cadinanos, et al., "Generation of an Inducible and Optimized piggyBac Transposon System," Nuc. Acids Res., 35 (12):Art. e87:1-8 (2007).
Chomzynski, et al. "Single-Step Method of RNA Isolation by Acid Guanidinium Thiocyanate-Phenol-Chloroform Extraction," Anal. Biochem., 162:156-159 (1987).
Cost, et al., "Targeting of Human Retrotransposon Integration is Directed by the Specificity of the L1 Endonuclease for Regions of Unusual DNA Structure" Biochemistry, 37:18081-18093 (1998).
Cost, et al., "Human L1 Element Target-Primed Reverse Transcription In Vitro," EMBO J., 21(21):5899-5910 (2002).
Deininger, et al., "Mammalian Retroelements," Genome Res., 12:1455-1465 (2002).
Dix, et al., "Hsp70 Expression and Function During Gametogenesis," Cell Stress & Chaperones, 2(2):73-77 (1997).
Feng, et al., "Human L1 Retrotransposon Encodes a Conserved Endonuclease Required for Retrotransposition," Cell 87:905-916 (1996).
Freundlieb, et al., "A Tetracycline Controlled Activation/Repression System With Increased Potential for Gene Transfer Into Mammalian Cells," J. Gene Med., 1:4-12 (1999).
Gilbert, et al., "Genomic Deletions Created Upon LINE-1 Retrotransposition," Cell 110:315-325 (2002).
Gish, et al., "Identification of Protein Coding Regions by Database Similarity Search," Nature Genet., 3:266-272 (1993).
Hakamata, et al. "Green Fluorescent Protein-Transgenic Rat: A Tool for Organ Transplantation Research," Biochemical and Biophysical Research Communications, BBRC 286:779-785 (2001).
Hampf, et al., "A Protocol for Combined Photinus and Renilla Luciferase Quantification Compatible With Protein Assays," Anal. Biochem., 356:94-99 (2006).
Han, et al., "A Highly Active Synthetic Mammalian Retrotransposon," Nature, 429:314-318 (2004).
Henikoff, et al. "Amino Acid Substitution Matrices From Protein Blocks," PNAS USA, 89:10915-10919 (1992).

(Continued)

*Primary Examiner* — Doug Schultz
(74) *Attorney, Agent, or Firm* — Norris McLaughlin & Marcus PA

(57) ABSTRACT

The invention relates to nucleic acids, vector constructs which allow the controlled activation and inhibition of retrotransposition of non-LTR retrotransposons. The methods of this invention are useful for preparing said nucleic acids and vector constructs and introducing them into cells.

26 Claims, 6 Drawing Sheets

(56) References Cited

OTHER PUBLICATIONS

Jurka, "Sequence Patterns Indicate an Enzymatic Involvement in Integration of Mammalian Retroposons,"PNAS USA 94:1872-1877 (1997).
Kay, et al., "Viral Vectors for Gene Therapy: The Art of Turning Infectious Agents Into Vehicles of Therapeutics," Nat. Med. 7(1):33-40 (2001).
Kimberland, et al., "Full-Length Human L1 Insertions Retain the Capacity for High Frequency Retrotransposition in Cultured Cells," Hum. Mol. Genet. 8(8):1557-1560 (1999).
Kistner, et al., "Doxycycline-Mediated Quantitative and Tissue-Specific Control of Gene Expression in Transgenic Mice," PNAS USA, 93:10933-10938 (1996).
Kubo, et al. "L1 Retrotransposition in Nondividing and Primary Human Somatic Cells," PNAS 103(21):8036-8041 (2006).
Lander, et al., "Initial Sequencing and Analysis of the Human Genome," Nature, 409:860-921 (2001).
Lavie, et al., "The Human L1 Promoter: Variable Transcription Initiation Sites and a Major Impact of Upstream Flanking Sequence on Promoter Activity," Genome Res., 14:2253-2260 (2004).
Lobe, et al., "Z/AP, A Double Reporter for Cre-Mediated Recombination," Dev. Biol., 208:281-292 (1999).
Lois, et al., "Germline Transmission and Tissue-Specific Expression of Transgenes Delivered by Lentiviral Vectors," Science, 295:868-872 (2002).
Luan, et al., "Reverse Transcription of R2Bm RNA is Primed by a Nick at the Chromosomal Target Site: A Mechanism for Non-LTR Retrotransposition," Cell, 72:595-605 (1993).
Madden, et al., "Applications of Network BLAST Server," Meth. Enzymol. 266:131-141 (1996).
Martin, et al., "Nucleic Acid Chaperone Activity of the ORF1 Protein From the Mouse LINE-1 Retrotransposon," Mol. Cell. Biol., 21(2):467-475 (2001).
Moran, et al. "High Frequency Retrotransposition in Cultured Mammalian Cells," Cell, 87:917-927 (1996).
No, et al., "Ecdysone-Inducible Gene Expression in Mammalian Cells and Transgenic Mice," PNAS, 93:3346-3351 (1996).
Ostertag, et al., "Biology of Mammalian L1 Retrotransposons," Annu. Rev. Genet., 35:501-538 (2001).
Prak, et al., "Tracking an Embryonic L1 Retrotransposition Event," Proc. Natl. Acad. Sci., 100:1832-1837 (2003).
Sambrook, et al., "The PCR Technique: DNA Sequencing," Molecular Cloning, 2nd ed., 9.47-9.58, Cold Spring Harbor Lab, press, Eds. J. Ellingboe and U. Gyllensten) (1989).
Sassaman, et al. "Many Human L1 Elements are Capable of Retrotransposition," Nat. Genet. 16:37-43 (1997).
Schmidt, et al., "Detection and Direct Genomic Sequencing of Multiple Rare Unknown Flanking DNA in Highly Complex Samples," Hum. Gene. Ther. 12:743-749 (2001).
Soifer, et al. "Stable Integration of Transgenes Delivered by a Retrotransposon-Adenovirus Hybrid Vector," Hum. Gene Ther. 12:1417-1428 (2001).
Soifer, et al., "Retrotransposon-Adenovirus Hybrid Vectors: Efficient Delivery and Stable Integration of Transgenes Via a Two-Stage Mechanism," Curr. Gene Ther., 4(4):373-384 (2004).
Sprengel, et al., "Tetracycline-Controlled Genetic Switches," Handbook of Experimental Pharmacology, Springer-Verlag Berlin Heidelberg,178:49-72 (2007).
Symer, et al., "Human L1 Retrotransposition Is Associated with Genetic Instability In Vivo," Cell, 110:327-338 (2002).
Tatusova, et al., "BLAST 2 Sequences—A New Tool for Comparing Protein and Nucleotide Sequences," FEMS Microbiol. Lett. 174:247-250 (1999).
Tchenio, et al., "Members of the SRY Family Regulate the Human LINE Retrotransposons," Nucl. Acids Res., 28(2): 411-415 (2000).
Thompson, et al., "Clustal W: Improving the Sensitivity of Progressive Multiple Sequence Alignment Through Sequence Weighting, Position-Specific Gap Penalties and Weight Matrix Choice," Nucleic Acids Res., 22 (22):4673-4680 (1994).
Witzgall, et al., "The Kruppel-Associated Box-A (KRAB-A) Domain of Zinc Finger Proteins Mediates Transcriptional Repression," PNA, 91:4514-4518 (1994).
Zingler, et al., Analysis of 5' Junctions of Human LINE-1 and Alu Retrotransposons Suggests an Alternative Model for 5'-end Attachment Requiring Microhomology-Mediated End-Joining, Genome Res., 15:780-789 (2005).
Reply to Written Opinion as filed on Jul. 15, 2010 in corresponding European Application No. 08 844 540.8.
First Examination Report dated Feb. 24, 2011 in corresponding European Application No. 08 844 540.8.
Reply to First Examination Report as filed on Jun. 16, 2011 in corresponding European Application No. 08 844 540.8.
Second Examination Report dated Aug. 4, 2011 in corresponding European Application No. 08 844 540.8.
Reply to Second Examination Report as filed on Sep. 5, 2011 in corresponding European Application No. 08 844 540.8.

Plate 1

Plate 2

1. Transfect M2 HeLa cells with Dox-inducible L1 reporter pteto7CMV/L1-3.blas.
2. Induce L1 transcription by adding Dox to medium.
3. Harvest cells and extract total RNA
4. Northern Blot analysis of Dox-induced L1-blast expression Time after dox-addition in hours

CONTROLLED ACTIVATION OF NON-LTR RETROTRANSPOSONS IN MAMMALS

CROSS-REFERENCE TO RELATED APPLICATIONS

This application is a U.S. national phase application of International Patent Application No. PCT/EP2008/009179, filed Oct. 30, 2008 which claims the benefit of EP 070213311.1, filed Oct. 31, 2007. The entirety of the aforementioned applications is herein incorporated by reference.

SEQUENCE LISTING

The instant application contains a corrected Sequence Listing which has been submitted in ASCII format via EFS-Web and is hereby incorporated by reference in its entirety. Said ASCII copy, created on Sep. 13, 2012, is named VOS-013.txt and is 9,258 bytes in size.

TECHNICAL FIELD

The invention relates to nucleic acids, vector constructs which allow the controlled activation and inhibition of retrotransposition of non-LTR retrotransposons. The methods of this invention are useful for preparing said nucleic acids and vector constructs and introducing them into cells.

BACKGROUND ART

Transposable elements are ubiquitous in higher eukaryotic genomes. Approximately 45% of the human genome are covered by transposable elements (Lander, E. S. et al. (2001) Nature, 409, 860-921). Transposable elements are DNA sequences that can be mobilized and spread to different positions within the genome of a single cell, a process called transposition. In the process, they can cause mutations and change the amount of DNA in the genome. Transposable elements are mobile genetic elements which are also called "jumping genes". There is a variety of mobile genetic elements, and they can be grouped based on their mechanism of mobilization. Class I mobile genetic elements, or retrotransposons, are transcribed into RNA, and then reverse transcribed and reintegrated into the genome, thereby duplicating the element ("copy & paste" mechanism). The major classes of retrotransposons either contain long terminal repeats at both ends (LTR retrotransposons) or lack LTRs and possess a polyadenylate sequence at their 3' termini (non-LTR retrotransposons). Class II mobile genetic elements are termed DNA transposons and are generally excised from one genomic site and integrated into another by a "cut & paste" mechanism.

The majority of transposable elements in mammalian genomes are retrotransposons, which are considered to transpose via an RNA intermediate. Of these, the largest group comprises non-LTR retrotransposons which cover ~42% of the human genome (Lander et al. 2001, Nature 409, 880ff). Long interspersed elements (LINES) are a major class of non-LTR retrotransposons and cover approximately 21% of the genome. LINE-1 retrotransposons (L1) cover about 17% of the human genome (Lander et al., 2001, Nature 409, 860-921) and play a significant role in shaping the mammalian genome, not only through their own expansion but also through the mobilization of non-L1 sequences. While the average haploid human genome harbors ~516,000 L1 copies, the subgroup of active L1s is fairly small, encompassing 80-100 elements (Sassaman et al., 1997, Nat. Genet. 16: 37-43; Brouha et al., 2003, PNAS 100: 5280-5285). So far, 82 retrotransposition-competent, full-length L1 elements were isolated and characterized (Sassaman et al., 1997, Nat. Genet. 16: 37-43; Brouha et al., 2003, PNAS 100: 5280-5285, Moran et al. 1996, Cell 87: 917-927; Kimberland et al. 1999, Hum. Mol. Genet. 8:1557-1560; Brouha et al. 2002; Am. J. Hum. Genet. 71: 327-336). L1s affected the genome by (i) insertion of truncated L1s into new sites, (ii) intrachromosomal homologous recombination between L1s, (iii) transduction of 3'-flanking sequences during retrotransposition, (iv) aiding trans generation of processed pseudogenes and retrotransposition of Alu elements, and (v) by causing genome instability through substantial deletions (Gilbert et al. 2002, Cell 110: 315-325; Symer et al. 2002, Cell 110: 327-338; Babushok & Kazazian, 2007, Human Mutation 28: 527-539).

A retrotransposition-competent, functional L1 element (RC-L1, FIG. 1) covers ~6.1 kb and contains a 5' untranslated region (5' UTR) with an internal and endogenous, CpG-rich promoter, a 1 kb ORF1 encoding a protein (p40) of ~40 kD with RNA-binding capability, followed by a 3.8 kb ORF2 coding for a protein (p150) with a predicted molecular weight of ca 150 kD with endonuclease (EN) and reverse transcriptase (RT) activities and a cysteine-histidine-rich domain. The 3'-end of L1 is terminated by a short 3' UTR, and a poly(A) tail (Ostertag & Kazazian, 2001, Annu. Rev, Genet. 35:501-538) (FIG. 1A). L1 mRNAs are atypical of mammalian RNAs because they are bicistronic and the mechanism of translation of L1 is not understood. The two ORFs are in frame and separated by a 63-bp noncoding spacer region. Mutational analyses demonstrated that both ORF1- and ORF2-encoded functional proteins are required for retrotransposition (Moran et al. 1996, Cell 87: 917-927; Feng et al. 1996, Cell 87: 905-916). At least three functions of the ORF2-encoded protein were shown to be essential for retrotransposition, RT activity, EN activity and a function associated with the cysteine-histidine-rich motif. Insertion of a new L1 copy into the loose genomic target sequence 5'-TTTT/A-3' (Gilbert et al. 2002, Cell 110:315-325; Feng et al. 1996, Cell 87: 905-916; Jurka, 1997, PNAS 94: 1872-1877; Cost & Boeke, 1998, Biochemistry 37:18081-18093) is initiated by a process termed target-primed reverse transcription (Luan et al. 1993, Cell, 72: 595-605; Cost et al. 2002, EMBO J. 21: 5899-5910). The structure of the target site duplications (TSDs) flanking de novo L1 integrants suggests a model for second strand synthesis of L1 termed "microhomology-driven single strand annealing" (Symer et al. 2002, Cell 110: 327-3389; Martin & Bushman, 2001, Mol. Cell. Biol. 21: 467-475).

While the majority of L1 and other L1-mediated insertions land in intergenic and intronic sequences with little or no consequence for their host, occasional insertions have disrupted gene expression and caused genetic disorders and cancer (for review Babushok & Kazazian, 2007; Human Mutation 28:527-539; Ostertag & Kazazian, 2006. Retrotransposition and Human Disorders. In: Encyclopedia of Life Sciences: John Wiley & Sons. Ltd: Chichester http://www.els.net/[doi: 10.1038/npg.els.0005492]. Of 53 known disease-causing insertions, 17 were caused by L1 itself, while L1-mediated integrations of Alu and SVA elements caused another 33 cases; three additional cases were caused by L1-mediated insertions of simple polyA repeats. For example, germ line L1 insertions into the factor VIII and dystrophin gene gave rise to hemophilia A and muscular dystrophy, respectively (Kazazian et al., 1988, Nature 332: 164-166; Narita et al., 1993, J. Clinical Invest. 91:1862-1867; Holmes et al., 1994, Nature Genetics 7:143-148). 16 somatic L1-mediated retrotransposition events caused a variety of cancers, including ALL1 rearrangement leukemias and BRCA1-associated familial breast cancer (Deininger & Batzer, 1999, Mol. Genet. Metab. 67: 183-193). Somatic L1 insertions into the c-myc and APC tumor suppressor gene were shown to be involved in breast and colon cancer, respectively (Morse et al., Nature 333:87-90; Miki et al., 1992, Cancer Research 52:643-645). Thus, L1 is a potential mutagen and L1 retrotransposition is mutagenic.

However, the controlled application of LINE-1 as a tool for random mutagenesis was hampered by the lack of an inducible system which allows temporally defined, quantitative and reversible regulation of high level LINE-1 retrotransposition in mammalian cells.

So far, only constitutive retrotransposition of marked LINE-1 reporter cassettes was achieved in mammalian cell lines and in germ cells or entire organism of transgenic animals (An et al., 2006, Proc. Natl. Acad. Sci., 103: 18662-7; Ostertag, 2002, Nat. Genet. 32: 655-60; Prak et al., 2003, Proc. Natl. Acad. Sci., 100: 1832-7; Babushok et al., 2006, Genome Ress., 16: 240-50). Also, LINE-1 mediated gene transfer was only performed with vectors expressing L1 constitutively (Kubo et al., 2006, Proc. Nad. Acad. Sci., 103: 8036-41; Soifer et al., 2001, Hum. Gene Ther., 12: 1417-28).

WO 88/03169 is merely concerned with constructs useful in yeast and describes a method for inducing retrotransposition of yeast Ty retrotransposons in yeast using the inducible GAL1 promoter which is not functional in mammalian cells. Ty elements are LTR retrotansposons that are functional in yeast whereas LINE-1s are non-LTR transposons which are functional in mammalian cells. Consequently, the disclosed techniques can not be transferred to mammalian cells.

Other methods relating to the constitutive expression of LINE-1s are known in the prior art. For example, US 2003/0121063 relates to a method for generating a mutation in the offspring of an animal. To achieve this goal, mice were transfected with different non-inducible LINE1 constructs and the offspring of these transgenic animals was analysed.

In addition, US 2006/0183226 discloses a new method the target-specific introduction of certain LINE-like retrotransposons (TRAS and SMART family members) into mammals. The use of inducible promoters is not described. The patent application US 2006/0183226 covers a similar field and describes several genetic modifications of LINE-1 to achieve sequence specific targeting with the modified construct.

The objective problem is to provide a vector construct and method which allows inducible, tightly controlled and conditional expression of functional tagged non-LTR retrotransposons, in particular, LINE-1 retrotransposons in mammals. The solution of this problem is the provision of a nucleic acid with a tetracycline-response element operably linked to a promoter which in turn is operably linked to a tagged LINE-1 element.

SUMMARY OF THE INVENTION

The present invention relates to a nucleic acid comprising in 5' to 3' direction (a) an inducible promoter operably linked with (b) a non-LTR retrotransposon, wherein the endogenous promoter of the non-LTR retrotransposon is genetically modified or removed to be inactive. Preferentially the inducible promoter comprises a tetracycline-response element (TRE) operably linked with (b) a promoter under control of the tetracycline-response element.

Another embodiment of the invention is a vector construct comprising the above-mentioned nucleic acid.

This vector may be a viral vector or a plasmid.

A method for preparing the above-mentioned nucleic acid or the above-mentioned vector construct are also within the scope of the invention.

In particular, the method for transfecting cells comprises the steps of providing a cell comprising a promoter and a nucleic acid sequence coding for a reversible Tet-transactivator-protein (rtTA) and expressing said rtTA, transfecting the cell with the vector construct, adding doxycyline and a selection agent to the cells, selecting for cells comprising the second marker, replacing the doxycyline and the selection agent with a selection agent selecting for cells comprising the first marker, and finally obtaining the selected cells.

The invention also relates to the use of the claimed vector construct to perform insertional mutagenesis or gene trapping in human cells, isolated mammalian cells, and non-human mammals.

It is also contemplated to use the claimed vector as a medicament, in particularly a gene-therapeutic medicament. The vector constructs of the invention may also be used for the preparation of a medicament for the treatment of cancer, metabolic diseases, cardiac diseases, or genetic disorders.

Figure 1:
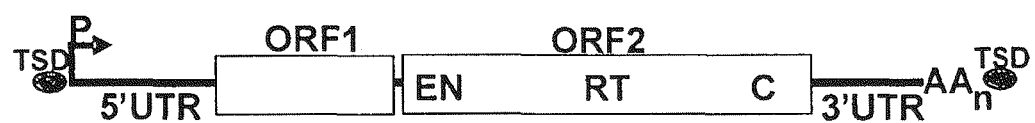
FIG. 1: Structure of a functional mammalian LINE-1 retrotransposon (For description see text) Abbreviations used are as follows: C, cystein-histidine-rich domain; TSD, target site duplications; UTR, untranslated region; RT, reverse transcriptase; AAAn, poly(A)tail; EN, endonuclease.

In order to generate a Doxycycline (Dox)-inducible L1 retrotransposition reporter construct using the Tet-On System, the L1.3 Retrotransposition reporter cassette (of a mblastI -or an EGFP-tag in its 3'UTR) was set under the control of the tetracycline-response-element (TRE) fused to the minimal CMV promoter ($P_{minCMV}$).

B, Schematic of the L1 retrotransposition reporter assay: The active L1 element was tagged with the indicator gene (black box in 3'UTR) containing an antisense copy of the basticidin-resistance gene (blast$^r$) disrupted by intron 2 of the gamma-globin gene in sense orientation (tsa-intron-lb) and inserted into the episomal pCEP4 vector. The splice donor (SD) and splice acceptor (SA) sites of the intron are indicated. The blast$^r$ gene is also flanked by a heterologous promoter ('P') and a polyadenylation signal ('A). Transcripts originating form the cytomegalovirus (CMV) promoter drive L1 expression and can splice the intron but contain an antisense copy of the blast$^r$ gene. G418-resistant (G418$^r$) colonies arise only if this transcript is reverse-transcribed, integrated into chromosomal DNA, and expressed from its own promoter P'. Annealing sites of oligonucleotide primers GS260 and Blast-B used to amplify sequences of de novo L1 integrants are indicated. Both primers are also used for "diagnostic" PCR of genomic DNA demonstrating de-novo retrotransposition: An 870-bp product is diagnostic for a spliced out intron and shows that retrotransposition of the tagged L1 reporter into the genome has occurred. In contrast, a 1770-bp product would come from the unspliced reporter gene cassette.

C, Experimental approach demonstrating that L1 retrotransposition occurs only after induction of L1 transcription by Dox; pTet07CMV/L1.3blas was transfected into 2×10⁵ HeLa-M2 cells/well expressing rtTA constitutively (Hampf and Gossen 2007, J. Mol. Biol. 365: 911-920) and Doxycyclin (Dox, 100 ng/ml) was added to wells 4, 5, 6, 10, 11, and 12 24 hours post transfection, HeLa-M2 cells were selected for the presence of the L1.3 retrotransposition reporter plasmid by adding 300 µg/ml Hygromycin (Hyg) to the medium in each well. Change of medium containing Hyg and Dox occurred every 48 hours. Wells 1-6 (Plate 1): Three days after transfection, Hyg and Dox were removed from the medium and transfected cells were selected for blasticidine-resistance (blast$^R$, 3 µg blasticidin/ml) to select for L1 retrotransposition events. Wells 7-12 (Plate 2): Five days after transfection, Hyg and Dox were removed from the medium and transfected cells were selected for blast$^R$.

In the absence of Dox, expression of the L1 reporter was not detectable in pTet07CMV/L1.3blas-transfected HeLa-M2 cells (Wells 1-3 and 7-9), which is indicated by the appearance of only sporadic blast$^R$ colonies. In contrast, the presence of Dox caused a massive activation of L1 retrotransposition events which is indicated by the growth of ~250 blase HeLa colonies per well (wells 4-6) in the case of three days of Dox induction, and ~550 blase HeLa colonies per well (wells 10-12) in the case of five days of Dox induction.

Abbreviations used are as follows: C, cystein-histidine-rich domain; TSD, target site duplications; UTR, untranslated region; RT, reverse transcriptase; AAAn, poly(A)tail; EN, endonuclease.

FIG. 3: A, Circular map of the episomal L1 retrotransposition reporter construct harbouring the inducible L1-3 element. The generation of the 674-bp probe specific for the Blast-gene is depicted.

B, Northern blot analysis of total RNA extracted from ptet07CMV/L1.3blas-transfected M2-HeLa cells. Cells were harvested before the addition of Dox (timepoint 0) and 6, 12 and 24 hours after Dox addition. The membrane was hybridized consecutively with L1-blast-specific and actin-gene-specific radiolabelled DNA probes.

DETAILED DESCRIPTION

Definitions

The terms used herein are well known in the art and have the meaning commonly known to the person skilled in the insofar as they are not defined hereafter:

The term "non-LTR retrotransposons" covers four subtypes, long interspersed nuclear elements (LINE-1s), short interspersed nuclear elements (SINEs), SVA elements (composite retrotranspsoson: SINE, VNTR, Alu), and LINE-like retrotransposons.

The term "autonomous non-LTR retrotransposons" relates to LINEs (Long interspersed nuclear elements) (Ostertag et al., "Biology of mammalian L1 retrotransposons", Annual Review of Genetics, 2001, vol. 35, 2001, pages 501-538.).

By "LINE1s" or "L1s" (Long interspersed nuclear elements) long DNA sequences (>5 kb, (King, Robert C. and William D. Stansfield (1997); A Dictionary of Genetics. Fifth Edition. Oxford University Press.)) are meant that represent reverse-transcribed RNA molecules originally transcribed by RNA polymerase II into mRNA (messenger RNA to be translated into protein on ribosomes) in mammals. LINE-1 elements code for 2 proteins; one that has the ability to bind single stranded RNA, and another that has known reverse transcriptase and endonuclease activity, enabling them to copy both themselves and noncoding SINEs such as Alu elements (see below for more detail).

Generally, a functional LINE-1 contains a 5'UTR (untranslated region) 2 ORFs (open reading frames) and a 3'UTR. In some embodiments of the invention the 5'UTR is not included in the nucleic acid or vector construct of the invention. The 5'UTR contains an internal polymerase II promoter sequence, while the 3'UTR contains a polyadenylation signal (AATAAA) and a poly-A tail (Deininger P L, Batzer M A. Mammalian retroelements. Genome Research. 2002; 12(10):1455-1465.). LINE1s are of mammalian origin. LINE1s in the preferred embodiments of the invention are of human, murine or rat origin. The nucleotide sequence for rat LINE1 is deposited at the NCBI nucleotide database (GenBank accession numbers: DQ100473-DQ100482).

By "retrotransposition" as used herein, is meant the process of transcription of a DNA sequence, reverse transcription of the resulting RNA sequence into a DNA by the LINE-1-encoded protein machinery and integration of the DNA into a genomic site.

By a "vector construct" as used herein, a sequence of DNA is referred to that will be propagated in eukaryotic or prokaryotic cell culture. Typical vectors are viral vectors or plasmids.

By "gene" as used herein, is meant an actual gene including both the exons and introns of the gene.

By "cDNA" as used herein, is meant a portion of a gene including only the exons of the gene.

By "selectable marker gene" as used herein is meant a gene or other expression cassette which encodes a protein which facilitates selection of cells into which the selectable marker gene is inserted or not inserted. Examples are genes coding for blasticidin-resistance, neomycin-resistance and others.

Selection can occur on the level of two events, first, the selection for successful transfection, second, the selection for successful retransposition. For selection of transfection a selectable marker gene can be placed outside the non-LTR retrotransposon cassette into the nucleic acid or vector including a promoter functionally linked to the selectable marker gene which is active in the cell that is to be transfected. After transfection/infection said selectable substance is added to the cell culture and only those cells will survive the treatment that have received at least one copy of said nucleic/acid vector. The second selectable marker having its own promoter can be placed into the 3' UTR of the non-LTR retrotransposon or any other part of the nucleic acid coding for the non-LTR retrotransposon as long as there is no interference with the retrotransposition event. The selectable marker and the promoter controlling its transcription may be in reverse direction to the promoter controlling the transcription of the non-LTR retrotransposon. To avoid transcription of the second selectable marker gene before retrotransposition the second selectable marker gene is interrupted by an intron, e.g. a small artificial gamma-globin intron or another intron. Thus transcription of the selectable marker gene before retrotransposition will result in a non-functional protein. The intron is constructed in a way that transcription of the cassette will lead to removal of the intron. The splice acceptor and donor sites are placed accordingly and as known in the state of the art. Only after reintegration of said transcribed cassette into the genome of the host the selectable marker gene can be expressed indicating the successful retrotransposition event.

By "reporter gene" as used herein is meant a gene or other expression cassette which encodes a protein which facilitates identification of cells into which the reporter gene is inserted. Examples are genes coding for 'Green Fluorescent Protein (GFP), Enhanced GFP (EGFP), β-Galactose.

By "host" is meant any biological system that supports retrotransposition events in the genome of the host. Such a biological system may be an animal, a mammalian animal, particularly a human. Cells, cell-lines or tissues derived from said animals are also regarded to be hosts.

By "therapeutic gene" as used herein is meant a gene or other expression cassette which encodes a protein or nucleic acid whose expression/transcription results in a therapeutic effect. The expression of the therapeutic gene may complement a gene that is not expressed in the host or in reduced amounts wherein the reduced or lacking expression of said host gene causes a disease or a disorder in the host. The therapeutic gene may also be a dominant negative mutant whose expression reduces or eliminates the effects of the expression of a host gene that causes a disease or genetic disorder in the host.

By "heterologous DNA" as used herein, is meant DNA which is not naturally found in the cell into which it is inserted or the nucleic acid into which it is inserted. For example, when mouse or bacterial DNA is inserted into the genome of a human cell, such DNA is referred to herein as "heterologous DNA". If a bacterial gene is inserted into mammalian or human retrotransposon, such DNA is referred to herein as "heterologous DNA". If a mammalian or human gene is inserted into mammalian or human retrotransposon and said mammalian or human gene is commonly not present in said retrotransposon, such DNA is referred to herein as "heterologous DNA". In contrast, the term "homologous DNA" as used herein, denotes DNA which is found naturally in the cell or nucleic acid into which it is inserted. For example, the insertion of mouse DNA into the genome of a mouse cell constitutes insertion of "homologous DNA" into that cell. In the latter case, it is not necessary that the homologous DNA be inserted into a site in the cell genome in which it is naturally found; rather, homologous DNA may be inserted at sites other than where it is naturally found, thereby creating a genetic alteration (a mutation) in the inserted site.

By "non-L1 DNA" as used herein, is meant DNA which does not naturally occur in an L1 element.

It will be appreciated that the invention should not be construed to be limited in any way to the precise DNA sequences which are disclosed herein. Homologous DNA sequences having substantially the same function as the disclosed DNA sequences are also considered to be included in the invention.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 8 out of 10, are matched or homologous, the two sequences share 80% identity. By way of example, the polypeptide sequences MCDEFG (SEQ ID NO: 4) and MCDHIK (SEQ ID NO: 5) share 50% identity and the nucleotide sequences GAATCG and GAAGAC share 50% identity. Nucleotide sequence identity can be determined using a known computer program. For example, amino acid or nucleotide sequences can be aligned by an alignment program such as CLUSTAL W (Thompson, et al., 1994, Nucleic Acids Res. 22:4673-4680), and identity can be calculated by counting the matching nucleotides. Gaps are treated in the same way as mismatches, and identity can be calculated as the ratio of matched nucleotides within the total number of nucleotides comprising the gaps. Alternatively, programs such as blastn can be used (Altschul, et al. (1990) J. Mol. Biol. 215:403-410; Gish, et al. (1993) Nature Genet. 3:266-272; Madden, et al. (1996) Meth. Enzymol. 266:131-141; Altschul, et al. (1997) Nucleic Acids Res. 25:3389-3402; Zhang, et al. (1997) Genome Res. 7:649-656). For example, in BLAST 2SEQUENCES, which compares two amino acid sequences or nucleotide sequences by blastp or blastn, respectively (see Tatusova et al. (1999) "Blast 2 sequences—a new tool for comparing protein and nucleotide sequences," FEMS Microbiol. Lett. 174:247-250; the NCBI website for BLAST 2 SEQUENCES [http://www.ncbi.nlm.nih.gov/blast/bl2seq/bl2.html]), BLOSUM62 is used as the matrix for scoring when comparing amino acid sequences (Henikoff, et al. (1992), "Amino acid substitution matrices from protein blocks," Proc. Natl. Acad. Sci. USA 89:10915-10919; Open gap penalty: 11, extension gap penalty: 1). Identity values can be obtained as Identities (%) by searching without the use of FILTER (filtering of Low-complexity sequences). In particular, nucleic acids having 99%, 98%, 97%, 96%, 95%, 90%, 80%, 70%, or 60% identity with the nucleic acids of the invention are claimed.

An "isolated DNA", as used herein, refers to a DNA sequence which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid (e.g., cellular components, RNA, DNA or protein) in its natural state. "Complementary", as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). The skilled person will also appreciate that artificial bases exist that can pair with natural occurring bases or with other artificial bases (e.g. phosphorothioate or PNA derived bases).

"Positioned in an antisense orientation with respect to the direction of transcription of the DNA" as used herein, means that the transcription product of the DNA, the resulting mRNA, does not encode the polypeptide product specified by the "sense" strand of DNA. Rather, the mRNA comprises a sequence which is complementary to an mRNA which encodes the protein product.

The term "insertional mutation" is used herein to refer the translocation of nucleic acid from one location to another location which is in the genome of an animal so that it is integrated into the genome, thereby creating a mutation in the genome.

A "retrotransposition event" is used herein to refer to the duplication of a retrotransposon sequence via a 'Copy & Paste' mechanism with the preferable outcome being integration of a new retrotransposon copy into a new genomic location. The genome is preferentially a mammalian or human genome.

The term "detecting the DNA molecule" is used herein to refer to methods well known in the art for identifying a specific nucleic acid sequence amongst other nucleic acid sequences, including but not limited to, PCR, RT-PCR, Southern hybridization, Northern hybridization, single strand conformation polymorphisms, and the like.

The term "cell" refers to any cell type. The cell can be part of an organism or isolated. Isolated cells are removed from the organism. Cells can be primary cells or cell-lines. Cells may be prokaryotic, preferentially eukaryotic, yet more preferentially mammalian and/or human.

The term "tissue" refers to any tissue type. The tissue can be part of an organism or isolated. Isolated tissues are removed from the organism. Tissues are preferentially from a mammalian and/or human source.

The term "promoter" relates to a specific DNA sequence that is recognized by proteins known as transcription factors. These factors bind to the promoter sequences, recruiting RNA polymerase, the enzyme that synthesizes the RNA from the coding region of the gene. In this way a gene is transcribed. Promoters can be active or inactive. In the former case transcription can occur starting from the promoter, in the latter case transcription of the gene does not occur. Activation/inactivation can occur if the promoter is under the control of operator sequence and certain factors are bound or not bound to the operator sequence activating/deactivating the promoter. An example for such a control mechanism is the 'Tet-System' explained below. Alternatively a promoter can be inactivated by genetically modifying the promoter, i.e. the nucleic acid sequence of a promoter that is usually constitutively active is altered in a way that transcription can no longer be initiated at said promoter. The promoter may be an exogenous promoter, i.e., a promoter that is not naturally found in non-LTR retrotransposons.

"Genetically modifying" relates to the replacement, addition, or deletion of nucleic acids in a nucleic acid sequence.

The term "codon optimized" or "codon optimized gene" relates to a gene in which the codons in a nucleic acid sequence of an open reading frame are altered to codons which are the most favored codons in highly expressed mammalian genes. However, the codons are altered without allowing a change of the encoded amino sequences. These altered "codon optimized" genes are especially useful for non-LTR retrotransposons, since in this way the transcriptional elongation defect which is reported to participate in the control of wildtype L1 retrotransposition frequency is bypassed (Feng et al. 1996, Cell, 87: 905-916; Moran et al. 1996, Cell: 917-927; Cost et al. 2002, EMBO J., 21: 5899-5910; Han and Boeke, 2004, Nature, 429: 314-318). As a consequence of the condon-optimization the transposition level of a non-LTR retrotransposon, in particular, a L1 retrotransponson or a genetically modified version of a L1 retrotransposon may increase by about 200-fold (Han and Boeke, 2004, Nature, 429: 314-318; An et al. 2006, PNAS, 103: 18662-7).

Nucleic Acids of the Invention

The nucleic acid of the invention may comprise, in 5' to 3' direction, an inducible promoter being operably linked with a non-LTR retrotransposon.

The non-LTR retrotranspon may be an autonomous non-LTR retrotranspon.

In a preferred embodiment, the nucleic acid of the invention may comprise in 5' to 3' direction a tetracycline-response element being operably linked with a promoter under control of the tetracycline-response element, and being operably linked with a non-LTR retrotransposon.

The promoter may be any promoter that can be controlled by a tetracycline-response element, in particular, the immediate-early promoter of cytomegalovirus. The tetracycline-response element may also be operably linked with the constitutive composite chicken β-actin promoter CAG (Lobe et al. 1999, Dev. Biol. 208: 281-292); the chicken β-actin promoter combined with the CMV immediate early enhancer (Hakamata et al.2001, BBRC 329: 288-295); the Ubiquitin-C promoter combined with CMV enhancer (Lois et al. 2002, Science 295: 868-872); the RNA-Polymerase II promoter; viral promoters, in particular the especially SV 40 promoter; house keeping promoter, in particular the actin-, PGK-, DNA polymerase II- and ubiquitin promoter; germ line-specific promoters, in particular, the mouse heat-shock protein 70-2 promoter (pHsp70-2), which is known to produce strong transgene expression in meiosis of male spermatogenesis (Dix et al. 1996, Dev. Biol. 174:310-321); the neuron-specific GnRH (gonadotropin-releasing hormone)-promoter.

In an alternative embodiment, the non-LTR retrotransposon is operably linked with an optimized ecdysone responsive promoter (No et al. 1996; Proc. Natl. Acad. Sci. USA 93: 3346-3351). The ecdyson-inducible expression system utilizes a heterodimer of the ecdyson receptor (VgEcR) and the retinoid X receptor that binds a hybrid ecdysone response element in the presence of the synthetic analog of ecdysone muristerone A (No et al. 1996; Proc. Natl. Acad. Sci. USA 93: 3346-3351). Binding of the heterodimer to the modified ecdysone response element in the minimal promoter, activates L1 transcription.

The non-LTR retrotransposon may further comprise a heterologous gene selected from the group consisting of a reporter gene, a therapeutic gene, and a selectable marker gene.

The reporter gene may be selected from the group consisting of GFP, β-Galactose.

An antisense GFP construct may be generated which replaces the $neo^R$ marker gene in the 3'-UTR of L1. As before, the initiation codon ATG of the GFP gene is replaced and a splice acceptor sequence is placed at the 5' end of the GFP gene. GFP expression will only occur if the gene product is expressed as an in-frame fusion protein. The N-terminus of this fusion protein is derived from the host gene into which the DNA inserted. A similar strategy can be used applying lacZ or composite indicator genes such as lacZ/$neo^R$ or GFP/$neo^R$. Furthermore, it is possible to generate three independent constructs to ensure that insertions can be identified in all three reading frames. A further heterologous gene may be the herpes simplex virus (HSV) thymidine kinase gene.

The selectable marker gene is selected from the group consisting of drug resistance genes, in particular the blasticidin resistance gene ($Blast^R$=blasticidin S deaminase), the neomycin resistance gene ($neo^R$=neomycin phosphotransferase), the hygromycin resistance gene ($hyg^R$), the puromycin resistance gene ($puro^R$), the zeocin resistance gene ($zeo^R$), the hgprt gene (=hypoxanthine guanine phosphoribosyl transferase, a human gene which can be selected for in human cells in culture).

The therapeutic gene may be a gene or other expression cassette which encodes a protein or nucleic acid whose expression/transcription results in a therapeutic effect. The expression of the therapeutic gene may complement a gene that is expressed in reduced amounts in the host or not at all wherein the reduced or lacking expression of said host gene causes a disease or a disorder in the host. The therapeutic gene may also be a dominant negative mutant whose expression reduces or eliminates the effects of the expression of a host gene that causes a disease or genetic disorder in the host.

The heterologous gene may be under control of a promoter and operably linked with this promoter which is different from the promoter controlling the transcription of the non-LTR retrotransposon. The nucleic acid sequence comprising the heterologous gene and the promoter operably linked to it may be in inverse direction to the promoter controlling transcription of the retrotransposon. This heterologous gene may also contain an intron. This intron may be designed to have splice donor and splice acceptor sequences which are in the same orientation as the transcriptional orientation of the L1 retrotransposon. The intron may be constructed in a way that if transcription starts at the heterologous gene's promoter, the resulting messenger RNA will be translated into a protein that is not functional. Not functional means that it does not have the function usually ascribed to the protein encoded by the heterologous gene. The promoter of the heterologous gene and the promoter of the retrotransposon may be the same or different. The promoter of the heterologous gene may be inducible or not inducible. If the promoter of the heterologous gene is also inducible it would be necessary to use a promoter that is different from the TRE-$P_{min}$ CMV promoter cassette which controls L1 transcription. This would facilitate to induce L1 transcription and expression of the heterologous gene independently from each other by different factors. That way it would be possible to trigger retrotransposition by adding Doxycyclin to the system, without affecting expression of the heterologous gene. Expression of the heterologous gene could then be induced at a desired later time point. This would be very advantageous if, e.g. a therapeutic or other gene is retrotransposed with the nucleic acid of the invention into a host, e.g. in a time- and/or tissue-specific way. Following L1 retrotransposition, expression of the heterologous, preferentially, therapeutic gene may be induced at a defined time point for a defined period of time. Thus, expression of a therapeutic gene or other treatment would be under a more efficient control than if only the retrotransposition process was regulated. Unnecessary transcription of the heterologous gene could be avoided.

Figure 2A:
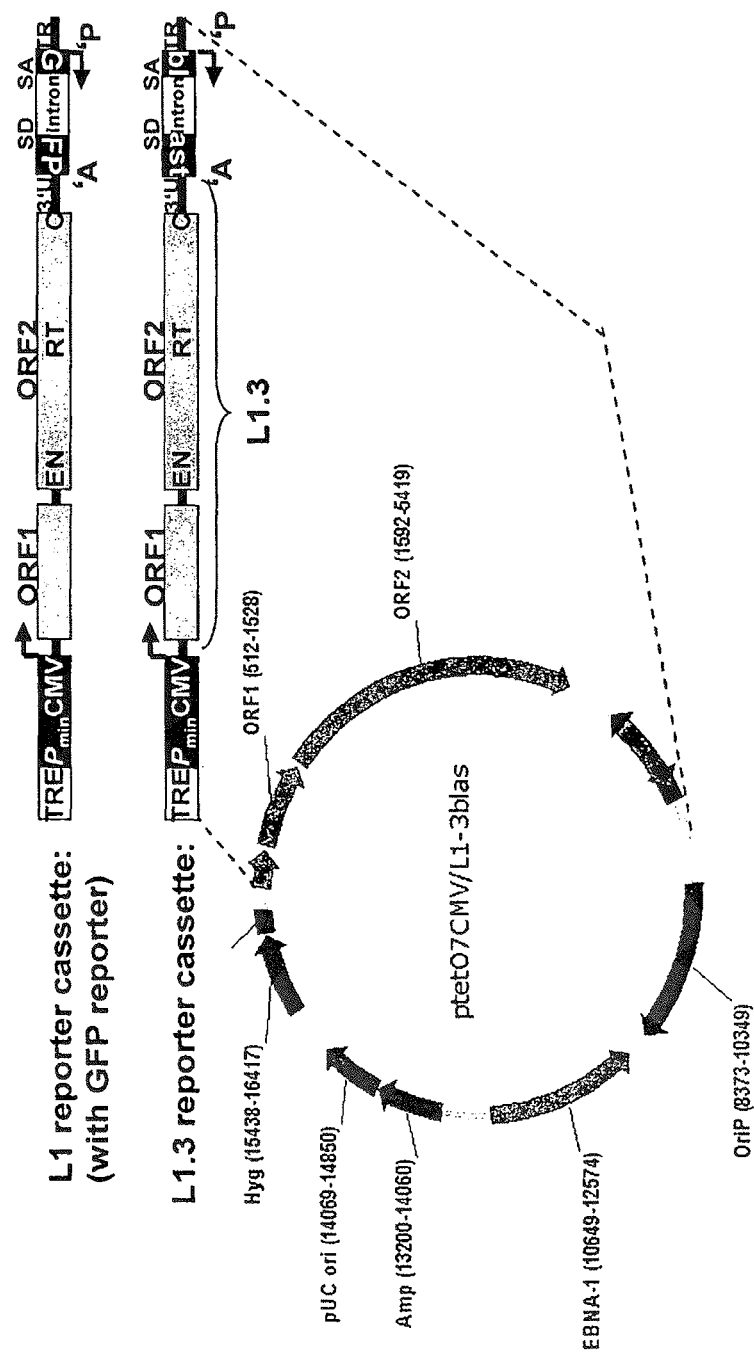
FIG. 2: A, Proof-of-Principle of inducible and tight on/off control of L1 retrotransposition applying the Tet-On system.

Referring to FIG. 2A, the promoter controlling the expression of the heterologous gene localized in the 3'-UTR region of L1 can be either an RNA Polymerase II—or an RNA-Polymerase III promoter. Examples of RNA Pol II promoters which are useful include, but are not limited to, housekeeping promoters, such as actin, PGK, DNA Pol III or a ubiquitin promoter; tissue-specific promoters, like albumin, globin, ovalbumin promoter sequences, skin specific promoters such as K12 or K14, inducible promoters, like steroid inducible promoters, the L1 element promoter, viral promoters, like SV40 early promoter, the Rous sarcoma virus (RSV) promoter and the cytomegalovirus immediate early promoter (CMV) and other retroviral LTRs. RNA polymerase III promoters which are within the scope of the invention are, tRNA promoters and the 5 S RNA promoter.

Additional promoters that may be used to control expression of the heterologous gene are: constitutive composite chicken β-actin promoter CAG (Lobe et al. 1999, Dev. Biol. 208: 281-292); chicken β-actin promoter combined with the CMV immediate early enhancer (Hakamata et al.2001, BBRC 329: 288-295); ubiquitin-C promoter combined with CMV enhancer (Lois et al. 2002, Science 295: 868-872); germ line-specific promoters like mouse heat-shock protein 70-2 promoter (pHsp70-2) known to produce strong transgene expression in meiosis of male spermatogenesis (Dix et al. 1996, Dev. Biol. 174:310-321); neuron-specific GnRH (gonadotropin-releasing hormone)-promoter.

It is also appreciated that both promoters are active in the same tissue and are the same or different promoters. Even tissue specific promoters may be leaky in the sense that retrotransposition may not occur in the intended tissue but also in other not intended tissues. The probability of leakage will be already reduced if the same two specific promoters are used. This would result in a more tissue specific expression of the heterologous or therapeutic gene. The specificity may even be increased by using two promoters which are specific for the same cell type or tissue but have different sequences, i.e. are of different types.

Figure 2B:
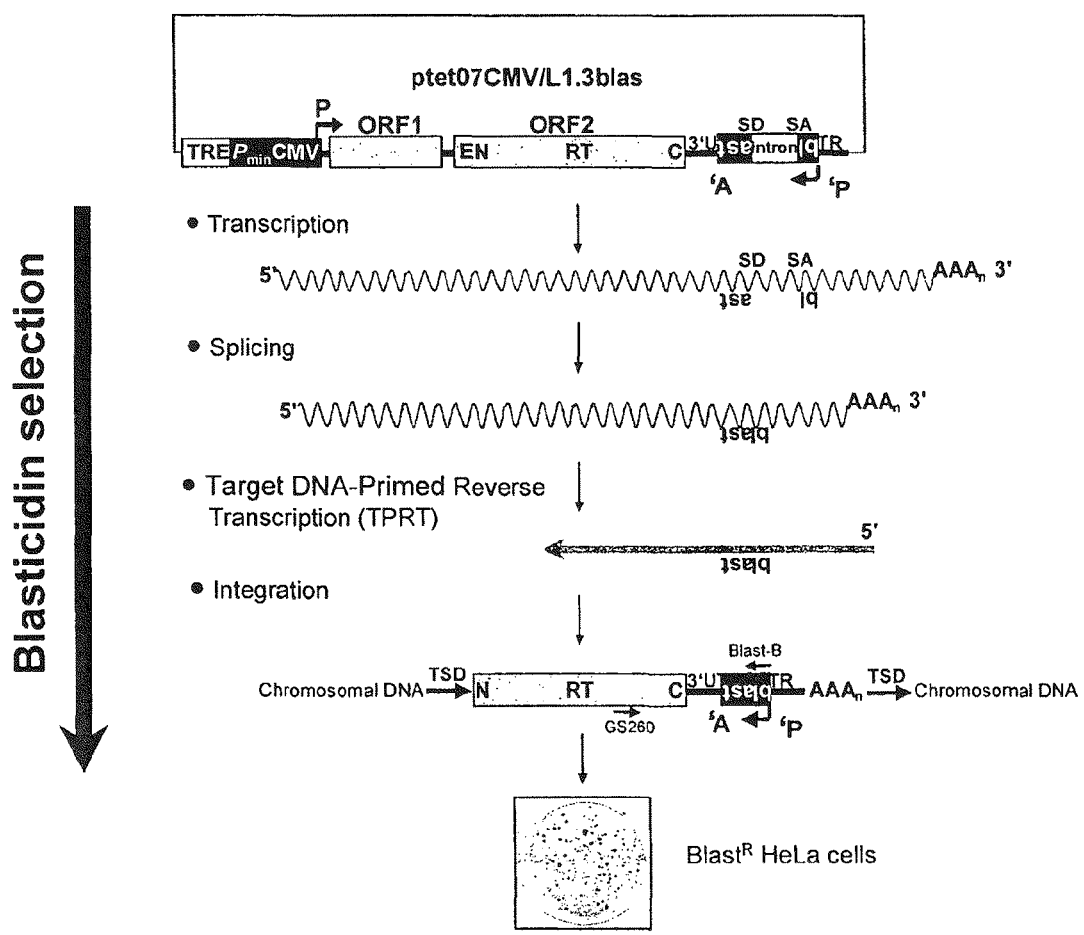
Figure 2C:
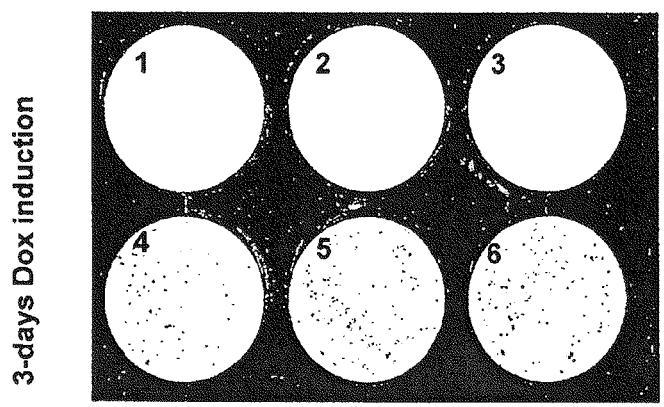
Figure 2C:
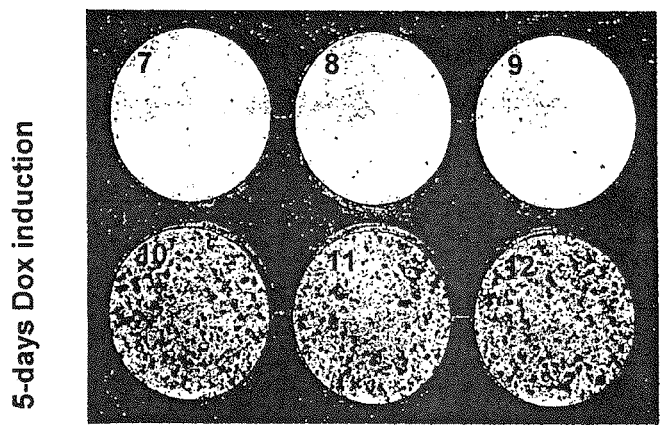

The non-LTR retrotransposon may be the mammalian long interspersed element 1 (LINE 1). The LINE-1 sequence may consist of a LINE-1 5' UTR, ORF 1, ORF 2, 3' UTR and a Poly A signal. The LINE-1 sequence may consist of a LINE-1 ORF 1, ORF 2, 3' UTR and a Poly A signal. The experimental data provided by the present inventors indicated that the endogenous promoter of the non-LTR retrotransposon needs to be inactivated in the nucleic acid of the invention in order to tightly control L1 transcription. It was surprisingly found that without such inactivation the non-LTR retrotransposon is constitutively transcribed even if operably linked to an inducible promoter. Thus transcription occurs independent of the activation/deactivation of the tetracycline-response element in the nucleic acid. Therefore, it was impossible to produce an inducible system for non-LTR retrotransposons using the techniques disclosed in the prior art. For rendering the non-LTR retrotransposon inducible it is therefore required to inactivate the endogenous promoter of the non-LTR retrotransposon. Inactivation of the promoter can be achieved in many ways, like genetically modifying the promoter sequence, in particular, by replacing the promoter sequence with any sequence that is not a promoter sequence in mammalian cells. Alternatively, the entire promoter region may be deleted. In a further alternative embodiment the 5'UTR of the non-LTR retrotransposon or of the LINE1 may be deleted. In the present invention it is essential to remove the promoter sequence, e.g., by removing the 5' UTR, to ensure that the regulation of L1 expression by the Tet-On system is tightly controlled (i.e, not leaky) and that the lack of Dox allows only sporadic and negligible L1 expression (FIG. 2C).

In a further embodiment of the invention the long interspersed element 1 (LINE-1) is selected from the group consisting of human, rat, and mouse LINE-1. In yet a further embodiment of the invention the mammalian long interspersed element 1 (LINE-1) is codon-optimized.

Vector Constructs of the Invention

Vector constructs of the invention may comprise any of the above recited nucleic acids of the invention.

The vector construct may be selected from the group consisting of a viral vector and a plasmid.

Viral vectors are well known in the art and be derived from any known vectors. Especially, vectors that can be used to transfer nucleic acids into mammalian, in particular, human cells, are appreciated.

The nucleic acids of the invention may be introduced into cells using viral vectors with a tropism for mammalian cells. The vector sequence may comprise DNA sequences derived from a virus, such as, but not limited to, Epstein Barr virus (EBV) comprising oriP and EBNA1 or a polyoma-based virus comprising the polyomavirus origin of DNA replication and a polyomavirus enhancer sequence. Other viral vectors useful in the invention include adenoviruss, adeno-associated virus, lentivirus, parvovirus, herpes simplex virus, retroviruses, poxviruses, and the like. These sequences comprise a eukaryotic origin of DNA replication to facilitate replication of the DNA molecule in a eukaryotic cell. Note, however, that certain vectors, such as adeno-associated virus, may be replication deficient, but may be still useful because they provide efficient delivery vehicles for introduction of the DNA into the desired target cell. It is not necessary that the vector sequences be limited to naturally occurring eukaryotic viral elements, e.g., mammalian artificial chromosomes are also contemplated in the invention.

The vector construct may contain a nucleic acid coding for a further selectable marker outside of the non-LTR retrotransposon, wherein said heterologous gene of the non-LTR retrotransposon will only be transcribed after the non-LTR retrotransposon has integrated into the genome of a cell.

The above-mentioned vectors may be constructed using known vector systems. By using viral vectors, the invented L1 expression cassette can be introduced efficiently into host cells, and RNAs and ORF-encoded proteins can be expressed at high levels. Those viral vectors that do not integrate into chromosomes are especially preferable. By using this type of vector, components necessary for retrotransposition can be transiently expressed in target cells. Since these vectors will be removed from cells over time, they will not be unnecessarily expressed after retrotransposition is complete, and are therefore vectors very useful in the present invention. Examples of viral vectors that do not integrate into chromosomes include adenovirus vectors (for example, pShuttle, Clontech), Sendai virus vectors, vaccinia virus vectors, Epstein-Barr virus vectors, baculovirus vectors, herpes virus vectors, and sindbis virus vectors (Soifer, H. et al., 2001, Hum. Gene Ther. 12: 1417-1428; Kay, M. et al., 2001, Nat. Med. 7: 33-40; Kubo et al. 2006, PNAS 103: 8036-41). By using a vector that integrates into chromosomes, the integration site may be regulated. Examples of vectors that integrate into chromosomes include retrovirus vectors, lentivirus vectors, adeno-associated virus vectors, and foamy virus vectors. These viral vectors can be prepared by methods well known to those skilled in the art. Viral vectors can be purified, for example, by centrifugation, according to their types.

In order to express the vectors of the present invention in animals, in vivo or ex vivo, DNA vectors such as plasmids can be administered together with transfection reagents such as cationic lipids or liposomes, e.g. Gene Juice (Novagen), FuGene (Roche). Naked DNAs or viral vectors can be directly administered. Examples for administration targets are humans and non-human mammals, and administration can be performed ex vivo or in vivo, to cells, tissues, organs, and such. Administration to a living body may be performed ex vivo or in vivo. In the case of in vivo applications, the vector of the present invention is administered directly to a living body. In the case of ex vivo applications, administration to cells outside a living body is followed by the introduction of those cells into a living body. As an example for an ex vivo method, cells producing a viral vector of the present invention may be administered.

Vector constructs in the sense of the invention is a nucleic acid including a vector as described above and an inducible non-LTR retrotransposon.

When administering locally to a target tissue, vector constructs or cells are administered to the target tissue via an injection needle, catheter, or such. Alternatively, vector constructs can be introduced to target tissues using carriers that can deliver vector constructs to specific tissues.

Thus, the vector constructs of the present invention can specifically facilitate L1 retrotransposition in tumor cells and such.

The vector constructs of the present invention can be mixed with known carriers and vehicles to form composites. The vector constructs of the present invention can also be administered as pharmaceutical compositions that are formulated by conventional preparation methods. For example, they can be prepared as compositions by mixing them with pharmaceutically acceptable carriers or vehicles, which specifically include sterilized water or physiological saline, salts, vegetable oil, stabilizers, preservatives, suspensions, and emulsifiers. Furthermore, the vector construct of the present invention can be prepared as compositions for introducing nucleic acids into cells together with liposomes or cationic lipids.

When administered as pharmaceutical agents to a living body, the vector constructs of the present invention can generally be administered locally or systemically by methods well known to those skilled in the art, such as intraarterial injection, intravenous injection, subcutaneous injection, and intramuscular injection. Alternatively, they can be administered locally through a syringe, catheter, needle-less injector, or such. Dosage can vary depending on a patient's weight and age, the method of administration, and the symptoms, but one skilled in the art can appropriately select an appropriate dose. Administration can be performed once, or a number of times. Administration of the vector constructs of the present invention can be performed according to conventional gene therapy protocols.

Methods of the Invention

A method of the invention relates to providing a cell comprising a nucleic acid of the invention as described above and inducing the transcription of the non-LTR. In a preferred embodiment, the method of the invention for transfecting cell culture cells comprises the steps of providing a cell comprising a nucleic acid comprising a promoter and a nucleic acid sequence coding for a tetracycline-controlled transactivator protein (tTA) and expressing said tTA or coding for a reverse tetracycline-controlled transactivator protein (rtTA) and expressing said rtTA, then transfecting the cell with the vector construct described above and adding doxycyline and a selection agent to the cells, wherein the selection agent positively selects cells expressing the selectable marker gene outside of the marked LINE-1 retrotransposon. Then a selection for cells comprising said selectable marker gene can be performed which is followed by replacing the doxycycline and the selection agent with another selection agent, wherein the selection agent positively selects cells expressing the heterologous marker gene localized in the 3'-UTR of the LINE-1 retrotransposon. Following this step the cells comprising the heterologous marker gene are selected. Finally, selected cells are obtained of at least one de-novo L1-retrotransposition event. In an alternative embodiment, the heterologous marker gene may be replaced or supplemented by a reporter gene, e.g., GFP. In that case, identification and possible selection of retrotransposed cells can occure visually, e.g., by inspection of cells in culture or inspection of tissues samples from animals.

In another embodiment expression of the reverse tetracycline-controlled transactivator-protein (rtTA) is replaced with the expression of the tetracycline-controlled transactivator-protein (tTA). In that case adding doxycycline is shutting down expression of the TRE-P$_{minCMV}$-controlled L1-retrotransposition reporter cassette (FIG. 1).

Further details of the application of the 'Tet-On' system in transgenic mice are summarized in Schonig & Bujard, "Generating conditional mouse mutants via Tetracycline-controlled gene expression", Methods in Molecular Biology, vol 209: pp 69-104, 2003 and in Sprengel & Hasan, "Tetracycline-controlled genetic switches", HEP, vol 178: 49-72, 2007, and c in Kistner et al., "Doxycyclin-mediated quantitative and tissue-specific control of the gene expression in transgenic mice", Proc. Natl. Acad. Sci. USA, vol. 93, pp. 10933-10938, 1996.

In a further embodiment the nucleic acid sequences coding for rtTA or tTA are functionally linked to a tissue-specific or ubiquitous, constitutively active promoter. In this way, the invention provides the benefit of providing a non-LTR retrotransposon that is not only inducible but will be induced only in desired tissues or defined cell types of the animal organism. This characteristic of the invention is very useful in transgenic animals when the expression of a nucleic acid is intended to be restricted to a particular pathologic tissue or cell type affected by disease. No expression would occur in healthy tissues and cell types of an animal. Thereby, undesirable side effects may be dramatically reduced. Alternatively, the promoter may be constitutive. For preparing such transgenic animals, an animal comprising the nucleic acid of the invention may be bred with an animal comprising a nucleic acid coding for rTA or rtTA, respectively.

In another embodiment the nucleic acid comprising a promoter and the nucleic acid sequence coding for the rtTA is provided by transfecting the cells with a vector containing said nucleic acid.

In yet another embodiment the nucleic acid comprising a promoter and the nucleic acid sequence coding for the tTA is provided by transfecting the cells with a vector containing said nucleic acid.

In another embodiment a cell is provided and the cell is co-transfected with the nucleic acid comprising a promoter and the nucleic acid sequence coding for the rtTA and one of the above defined vector constructs encoding the Tet/Dox-inducible L1 reporter cassette.

In yet another embodiment a cell is provided and the cell is co-transfected with the nucleic acid comprising a promoter and the nucleic acid sequence coding for the tTA and one of the above defined vector constructs encoding the Tet/Dox-inducible L1 reporter cassette.

The Tet System

The Tet system exists in the form of the Tet-Off and the Tet-On System:

In the Tet-Off System the tetracycline-response element (TRE) is located upstream of the minimal immediate early promoter of cytomegalovirus (P$_{minCMV}$), which is silent in the absence of activation. tTA (Tetracycline-controlled transactivator) binds the TRE—and thereby activates transcription of the LINE-1 retrotransposon—in the absence of Dox;

In the Tet-Off system, tTA binds the TRE and activates LINE-1 transcription in the absence of tetracycline or Dox.

In the Tet-On System the 'reverse' Tet repressor (rTetR) was created by four amino acid changes of the Tet repressor that reverse the protein's response to Dox. As a result of these changes, the rTetR domain of the reversible Tet-transactivator (rtTA=fusion of rTetR and the C-terminal 127 amino acids of the Herpes simplex virus VP16 activation domain) binds the TRE and activates transcription of the L1 reporter cassette in the presence of Dox. In a preferred embodiment, the gene of interest is the L1 retrotransposition reporter cassette.

In the Tet-On system, rtTA binds the TRE and activates transcription of LINE1 in the presence of Dox (see also Clontech, Tet systems user manual, 2007).

In a further embodiment of the invention, the nucleic acid which contains an inducible promoter pursuant to the Tet-On system is combined with a tetracycline-controlled transcriptional silencer. If the Tet-On system is used for induction of the tetracycline-controlled, conditional LINE-1 (L1) retrotransposition in mammalian cells, the system can be combined with a tetracycline-controlled transcriptional silencer (tTS) to minimize the background expression in absence of doxycycline (Dox). tTS is a fusion protein of the tet repressor (TetR) and the KRAB-AB silencing domain of the Kid-1 protein, a powerful transcriptional repressor (Freundlieb S. et al. 1999, J. Gene Med. 1: 4-12; Witzgall R. et al. 1994, Proc. Natl. Acad. Sci USA 91: 4514-4518). In the absence of Dox, tTS binds to the tetO7 sequence in the tet responsive element (TRE) of the otetO7CMV/L1.3bblas and blocks expression and thus retrotransposition of the L1 element. In the presence of Dox, the tTS dissociates from the TRE, allowing the Dox dependent binding of rtTA to the TRE and activating the expression of L1.

Alternative Systems with Inducible Promoters

In an alternative embodiment, the non-LTR retrotransposon is operably linked with an optimized ecdysone responsive promoter (No et al. 1996; Proc. Natl. Acad. Sci. USA 93: 3346-3351). The ecdyson-inducible expression system utilizes a heterodimer of the ecdyson receptor (VgEcR) and the retinoid X receptor that binds a hybrid ecdysone response element in the presence of the synthetic analog of ecdysone muristerone A (No et al. 1996; Proc. Natl. Acad. Sci. USA 93: 3346-3351). Binding of the heterodimer to the modified ecdysone response element in the minimal promoter, activates L1 transcription.

Targeted Integration of Tet/Dox-Inducible Marked L1 Elements

Mammalian wildtype LINE-1s integrate randomly into the consensus insertion sequence 5'-TTTT/A-3' into the host genome. To achieve site specific insertion of DNA into the host genome, a gene coding for a sequence-specific or protein-specific DNA-binding domain may be positioned somewhere within the L1-coding sequence. The specific domain may include a p53 binding domain, a zinc finger binding domain, type II endonuclease binding domain, a homeobox binding domain, APE-type endonucleases, and other domains. In this way, the mammalian LINE-1 retrotransposons can be directed to areas next to genes that are controlled by the above-mentioned factors or to genomic regions where de-novo L1 integration is not harmful to the host cell (cf. US2006/0183226, page 1 et seq.).

Isolation of Host-Encoded Genes Flanking the De-Novo L1 Insertion Site

In order to facilitate the isolation of host genes flanking the insertion site the L1 cassette may be modified in a way so that it contains an origin of replication (ori), e.g. prokaryotic on or eukaryotic on (yeast oris, like 2 micron, or ARS/CEN and others) in the 3' UTR region or between the start of the 3' UTR and the polyA signal. Independent of such modification, after a successful de-novo L1 retrotransposition event the host-genome DNA can be digested with a restriction enzyme cleaving outside of the cassette or a region thereof. Subsequently the isolated host genome DNA may be religated and propagated in prokaryotic or eukaryotic cells depending on the selected on (cf. US2006/0183226, page 9, section 80).

Gene-Trap Technology

The claimed constructs and methods can also be combined with gene-trap technology. For example, the promoter and initiation codon are eliminated and an intron acceptor splice site is added in place thereof. After retrotransposition the heterologous marker gene may be placed 3' to a host gene controlled by a host promoter. Thus, the heterologous (marker) gene can only be expressed as a fusion protein. Naturally, this specific method will only detect expressed host genes and allow the detection of insertional mutations in or close to expressed genes.

For example, a selectable marker gene can be introduced into the 3' UTR as described above. The promoter driving expression of said selectable marker gene is removed and a splice acceptor signal is inserted at the start codon of the selectable marker gene; a bacterial promoter (which is only transcribed in bacteria) driving expression of a marker selectable in bacteria and an origin of replication, are introduced downstream of the indicator gene. If the LINE-1 element retrotransposes into a desired region of the genome (site specific or not site specific), the selectable marker gene is spliced into mRNA. If the splicing event places the selectable marker gene in frame with the preceding exons, the selectable marker gene mRNA is translated and cells expressing the marker can be selected. Three different constructs may be designed such that all three reading frames of marker DNA are read thereby ensuring expression of protein from any spliced mRNA. The presence of the bacterial promoter and origin of replication downstream of the indicator gene should not interfere with splicing, but will allow for the simple isolation of the retrotransposed genomic LINE-1 retrotransposon insertions using methods similar to those described herein.

This strategy can also be used for the production of specific knock-out mutants via L1 insertion.

The "marker-gene" will then be an antisense sequence of the gene to be knocked out resulting in a hairpin structure that cannot be transcribed.

Alternatively, a "promoter trap" can be constructed by providing an indication gene with an initiation codon but lacking a promoter. The indication gene will be detectable if the cassette is integrated close to an active promoter which can then be identified.

An "enhancer trap" can also be designed by combining the L1 cassette with an indicator gene of an initiation codon and a weak promoter that does not lead to transcription without the presence of any enhancer.

Detection of De-Novo L1 Retrotransposition Events

De-novo LINE-1 insertions retrotransposed by the methods of the present invention can be detected by Southern blot analysis of host chromosomal DNA, by in situ hybridization of chromosomes such as FISH, or by 'Extension Primer Tag selection' (EPTS)-LM-PCR (Schmidt et al. 2001, Hum. Gene. Ther. 12: 743-49) or Inverse PCR (An et al. 2006, PNAS, 103:18662-18667). The polymerase chain reaction (PCR) which is well known in the art can also be used to detect retrotransposition events (Sambrook, J et al., Molecular Cloning $2^{nd}$ ed., 9.47-9.58, Cold Spring Harbor Lab. press, 1989; "The PCR Technique: DNA sequencing" (Eds. J. Ellingboe and U. Gyllensten), "BioTechniques Update Series", Eaton Publishing, 1999; "The PCR Technique: DNA sequencing II" (Eds. U. Gyllensten and J. Ellingboe), "BioTechniques Update Series", Eaton Publishing, 1999; "PCR Technology: principles and application for DNA amplification" Ed. by H. A. Erlich, 1989, Stockton Press).

By using primer pairs for the PCR analyses that are specific for the heterologous gene positioned within the 3' UTR, it is possible to distinguish a genomic, spliced and retrotransposed copy of the L1 reporter element from an unspliced original L1 cassette of our invention (FIG. 2A). Genomic sequences flanking de-novo L1 insertions can be identified by EPTS-LM-PCR (Schmidt et al.2001, Hum. Gene. Ther. 12: 743-49) or Inverse PCR (An et al. 2006, PNAS, 103: 18662-18667).

Advantages of The Invention

1. In the case of transient cotransfections performed in cell culture experiments:
   The ability to induce L1 retrotransposition for a defined period of time makes it possible to avoid consecutive transfections in order to evaluate the effect of certain gene products on L1 retrotransposition. Series of consecutive transfections produce more stress for transfected cells than a single transfection event and can cause secondary effects influencing the outcome of an experiment. The vectors and nucleic acids of the invention allow the cotransfection of an expression construct whose gene product may have an impact on L1-retrotransposition with an L1 reporter construct to induce L1 expression precisely for the period of time, the expression of the concurrently transfected expression construct is detectable.
2. This invention will permit conditional expression of a functional tagged L1 retrotransposon in double transgenic mice/rats, i.e. L1 expression can reversibly be adjusted in a time-dependent and dose-dependent manner. A mouse model applying the invention allows to monitor retrotransposition frequency in defined tissues and cell types during defined periods of development.
3. In the case of an ex vivo gene therapeutic approach using L1 retrotransposons as gene delivery system, the time point of expression of the therapeutic gene into the host genome can be controlled by controlling the time point of retrotransposition of the L1-based gene delivery vector.

INDUSTRIAL APPLICABILITY

The herein disclosed nucleic acids, vectors and methods have industrial applications.

1. The present invention facilitates random insertional mutagenesis in cells and transgenic organisms in defined tissues and during well defined and controlled periods of time. The tightly controlled activation and deactivation of L1 retrotransposition at defined time points facilitates the identification of gene functions in general and at defined developmental stages. Conditional activation of the L1 retrotransposition in defined somatic tissues will help to identify genes involved in cancer development. The relevance for the pharmaceutical industry is obvious.
2. Ex vivo gene therapy approaches with L1/Adenovirus-Hybridvectors or with other L1-based gene delivery systems: If the therapeutic gene is part of the inducible controlling the time point of L1 retrotransposition will define the start of therapeutic gene expression. In order to be introduced into the cell, the inducible L1-cassette of the therapeutic gene has to be combined with an infectious virus.

The invention can be used to identify the effects of host-encoded or other proteins or components on L1 retrotransposition activity (which causes mutations that can lead to genetic disorders or cancer) in tissue culture cells. L1 transcription will be upregulated for the period of time the host gene of interest is expressed in the cell. This way it is guaranteed that L1 expression and L1 transcription occurs only in the presence of the gene product of interest.

EXAMPLES

Example 1

General Experimental Approach:

- Transfection of $2 \times 10^5$ HeLa-M2 cells with ptetO7CMV/L1.3blas (add doxycyclin [100ng/ml] to medium in wells #4,5 and 6~30 min prior to transfection)

-add hygromycin (300mg/ml) ~24 h post-transfection;
-renew Dox-containing medium every 2 days until day 5;

-stop hygromycin selection, remove dox and start blasticidin selection (3mg/ml) at 5 days after transfection;

-Stain HeLa-M2 colonies with Giemsa after 8 days of blasticidin selection

Detailed Experimental Protocol

M2-HeLa cells (Hampf & Gossen, 2006, Anal Biochem.; 356(1):94-9) were used together with the inducible L1-retrotransposition-reporter-plasmid ptetO7CMV/L1.3blas (FIG. 2A). M2-HeLa cells express the transactivator-protein rtTA. The cells were cultivated in D-MEM (BIOCHROM AG) with 4.5 g glucose (SIGMA), 10% FCS (BIOWEST), 2 mM glutamine (BIOCHROM AG), and 250 µg geneticine/ml (GIBCO or INVITROGEN) at 37° C. and 5% $CO_2$. $2 \times 10^5$ M2-HeLa cells were seeded per well of a six-well plate. 24 hours later the cells were incubated with the transfection reagent GeneJuice (Novagen) containing 1 µg ptetO7CMV/L1.3blas (16976 bp) according to the instructions of the manufacturer. Concurrently, doxycycline (Dox, final concentration 100 ng/ml) (SIGMA) were added to the medium. 24 hours after the addition of ptetO7CMV/L1.3blas the selection of transfected cells was initiated by adding hygromycin (final concentration, 300 µg/ml) (INVITROGEN) to the medium. Control samples contained neither hygromycin nor doxycycline. Every 48 hours the medium was replaced by fresh medium containing the above cited concentrations of doxycycline and hygromycin. Three and five days after transfection of the vector construct, selection with hygromycin and the addition of doxycycline were terminated and a selection for retrotransposition events was started by adding blasticidine at a final concentration of 3 µg/ml (FIG. 2C). Transfected cells that were grown in the absence of Dox resulted in only sporadic blasticidine resistant colonies (FIG. 2C, wells 1-3 and 7-9) indicating that L1 was barely expressed and only sporadic L1 retrotransposition events took place. Strikingly, adding dox to the cells for three and 5 days led to a massive activation of L1-retrotransposition, which is reflected by ~250 (FIG. 2C, well # 4-6) and ~550 (FIG. 2B, well #10-12) blasticidine-resistant HeLa colonies, respectively. The experiment demonstrates 'proof-of-principle' of temporal control of L1-retrotransposition by adding Dox to the medium.

Example 2

The system described in example 1 is used to analyse the role of double-strand break (DSB) repair enzymes during L1-retrotransposition. Dominant negative mutants, shRNA constructs, and siRNA acting on said enzymes or on the expression of said enzymes are used to influence the activity/expression of these enzymes. The Tet-On/Off system can be used to activate L1-retrotransposition only during the time period the DSB repair enzymes are influenced in the above described way. In this way, only those L1 retrotransposition events are analyzed that took place in the presence of the modified DSB repair protein expression.

Example 3

Figure 3A:
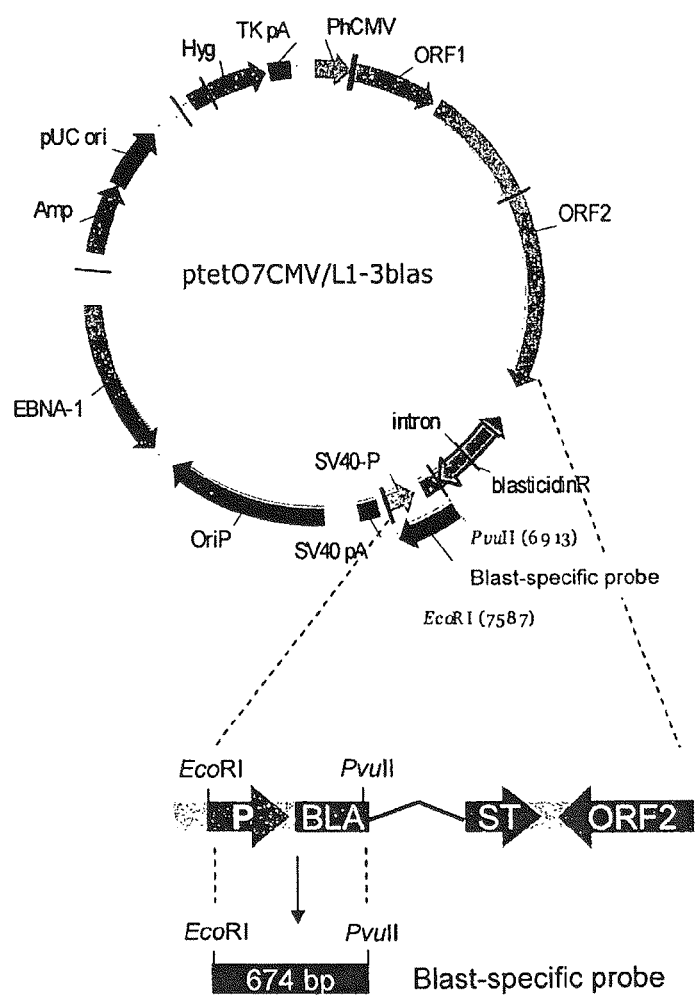
Figure 3B:
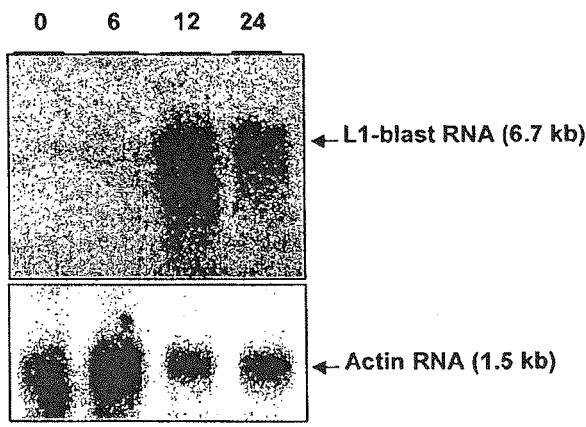

Timecourse Experiment Demonstrating Induction of L1 Expression Over Time after Dox-Addition.
Four T75-flasks containing $6 \times 10^6$ M2-HeLa cells in DMEM-Medium each were transfected with 6 µg of the inducible L1 reporter plasmid ptetO7CMV/L1.3blas (FIG. 3A).
One day after transfection, transfected M2-HeLa cells were selected for the presence of the inducible L1 reporter construct by adding hygromycin (final conc. 300 µg/ml) to the growth medium.
DMEM medium containing hygromycin was changed twice a week.
After 17 days of hygromycin selection, ptetO7CMV/L1.3blas-containing cells were harvested and cells were dispersed on eight 10-cm dishes with $1.7 \times 10^6$ cells per dish.
With the exception of two plates, doxycyclin was added to each plate to a final concentration of 200 ng/ml to induce transcription of the L1-reporter element localized on ptetO7CMV/L1.3blas.
Cells were harvested 0, 6, 12 or 24 hours after dox-addition. For each timepoint, $3.4 \times 10^6$ cells (two plates) were harvested and total RNA was extracted (FIG. 3B) using the 'Single-Step RNA Isolation Method' described recently (Chomzynski & Sacchi, 1987. Anal. Biochem. 162: 156-9).
For each time point before and after dox-induction, 15 µg of denatured total RNA were subjected to electrophoresis in a horizontal 1.2% agarose gel containing morpholinepropane sulfonic acid (MOPS) buffer and 6% formaldehyde (Sambrook et al. 1989, Molecular Cloning: a laboratory manual, 2nd ed. Cold Spring Harbor Laboratory Press, Cold Spring Harbor, N.Y.).
Subsequently, the RNA was transferred to a nylon membrane by the Northern blot procedure (FIG. 3B).
The probe used to detect inducible L1 transcripts was a 674-bp PvuII-EcoRI fragment covering the 5'-half of the blasticidin-gene (Blast) in the reporter cassette (FIG. 3A). Transcription of the constitutively expressed actin gene was detected with the help of a 643-bp fragment of the actin cDNA generated by PCR with oligonucleotides SW38 (5'- CACCCACAACGTGC-CCATTTATGAG-3' (SEQ ID NO: 2)) and SW39 (5'-TTTGCGGTGGACGATGGAAGG-3' (SEQ ID NO: 3)). The DNA probes were labelled for hybridization with ($\alpha$32P)dATP by random priming (Feinberg & Vogelstein, 1983, Anal. Biochem. 132:6-13).
Result: Induction of L1-blast transcription occurred between 6 and 12 hours after Dox-addition (FIG. 3B). L1-blast expression is slightly reduced after 24 hours due to the instability of Doxycyclin (Barry and Badal, 1978, Current Microbiology, 1:33-36) and because it is consumed by the cells over time.

The invention claimed is:

1. A nucleic acid molecule comprising:
an autonomous non-long terminal repeat (LTR) retrotransposon that lacks an intact endogenous promoter; and an operably linked inducible first promoter exogenous to the retrotransposon.

2. The nucleic acid molecule of claim 1, wherein the first promoter comprises a tetracycline-response element (TRE) operably linked to a TRE-responsive promoter.

3. The nucleic acid molecule of claim 2, wherein the TRE-responsive promoter is a cytomegalovirus promoter.

4. The nucleic acid molecule of claim 1, wherein the retrotransposon comprises a heterologous gene selected from the group consisting of a reporter gene, a therapeutic gene, and a selectable marker gene.

5. The nucleic acid molecule of claim 4, wherein the reporter gene is selected from the group consisting of a green fluorescent protein (GFP) gene, an enhanced-GFP (EGFP) gene, and a beta-galactose gene.

6. The nucleic acid molecule of claim 4, wherein the selectable marker gene confers resistance to an antibiotic.

7. The nucleic acid molecule of claim 6, wherein the antibiotic is selected from the group consisting of blasticidin and neomycin.

8. The nucleic acid molecule of claim 4, wherein the heterologous gene is operably linked to a second promoter.

9. The nucleic acid molecule of claim 8, wherein the first and second promoters are not the same promoter.

10. The nucleic acid molecule of claim 8, wherein at least one of the first and second promoters is selected from the group consisting of a tissue-specific promoter and a cell-type specific promoter.

11. The nucleic acid molecule of claim 8, wherein the second promoter is an inducible promoter.

12. The nucleic acid molecule of claim 1, wherein the retrotransposon comprises a mammalian retrotransposon ORF1, ORF2, 3' UTR, and poly A signal.

13. The nucleic acid molecule of claim 12, wherein the mammal is selected from the group consisting of a human, a rat, and a mouse.

14. The nucleic acid of claim 12, wherein the retrotransposon is a mammalian long interspersed element 1 (LINE-1) type retrotransposon.

15. The nucleic acid molecule of claim 14, wherein the LINE-1 is codon optimized.

16. The nucleic acid molecule of claim 12, comprising a heterologous gene in the 3' UTR, the heterologous gene being selected from the group consisting of a reporter gene, a therapeutic gene, and a first selectable marker gene.

17. The nucleic acid molecule of claim 16, wherein the reporter gene is selected from the group consisting of a green fluorescent protein (GFP) gene, an enhanced-GFP (EGFP) gene, and a beta-galactose gene.

18. The nucleic acid molecule of claim 16, wherein the selectable marker gene confers resistance to an antibiotic.

19. The nucleic acid molecule of claim 16 wherein the heterologous gene in the 3' UTR can be transcribed only after retrotransposition of the retrotransposon.

20. The nucleic acid molecule of claim 16, wherein the heterologous gene is operably linked to a second promoter.

21. The nucleic acid molecule of claim 20, wherein the first and second promoters are not the same promoter.

22. The nucleic acid molecule of claim 20, wherein at least one of the first and second promoters is selected from the group consisting of a tissue-specific promoter and a cell-type specific promoter.

23. The nucleic acid molecule of claim 1, wherein the molecule is a vector construct selected from the group consisting of a viral vector and a plasmid.

24. The nucleic acid molecule of claim 20, wherein the heterologous gene is positioned in the retrotransposon 3' UTR such that it can be transcribed only after retrotransposition of the retrotransposon into a cell genome and wherein the molecule further comprises, outside of the retrotransposon, a second selectable marker gene.

25. A method for transfecting mammalian cells comprising the steps of: transfecting into a mammalian cell that expresses a reverse tetracycline-controlled transactivator-protein (rtTA) a nucleic acid molecule that comprises:

an autonomous non-long terminal repeat (LTR) retrotransposon having a mammalian retrotransposon ORF1, ORF2, 3' UTR and poly A signal but lacking an active endogenous promoter, an inducible first promoter exogenous to and operably linked to the retrotransposon, a first selectable marker gene exogenous to the retrotransposon, and a second selectable marker gene provided in the 3' UTR and operably linked to a second promoter; exposing the transfected cells to doxycycline and a first selection agent that positively selects cells expressing the first selectable marker, for a time sufficient to select the cells expressing the first selectable marker;

exposing the selected cells to a second selection agent that positively selects cells expressing the second selectable marker, for a time sufficient to select the cells expressing the second selectable marker; and recovering the cells selected in step (c).

26. The method of claim 25, wherein the mammalian cells are of human origin.

* * * * *

SEQUENCE LISTING

<160> NUMBER OF SEQ ID NOS: 5

<210> SEQ ID NO 1
<211> LENGTH: 6059
<212> TYPE: DNA
<213> ORGANISM: Artificial Sequence
<220> FEATURE:
<223> OTHER INFORMATION: Description of Artificial Sequence: Synthetic
      TET controlled L-1 polynucleotide

<400> SEQUENCE: 1

| | | | | | | |
|---|---|---|---|---|---|---|
| gggggaggag | ccaagatggc | cgaataggaa | cagctccggt | ctacagctcc | cagcgtgagc | 60 |
| gacgcagaag | acggtgattt | ctgcatttcc | atctgaggta | ccgggttcat | ctcactaggg | 120 |
| agtgccagac | agtgggcgca | ggccagtgtg | tgtgcgcacc | gtgcgcgagc | cgaagcaggg | 180 |
| cgaggcattg | cctcacctgg | gaagcgcaag | gggtcaggga | gttccctttc | tgagtcaaag | 240 |
| aaaggggtga | cggtcgcacc | tggaaaatcg | ggtcactccc | acccgaatat | tgcgcttttc | 300 |
| agaccggctt | aagaaacggc | gcaccacgag | actatatccc | acacctggct | cggagggtcc | 360 |
| tacgcccacg | gaatctcgct | gattgctagc | acagcagtct | gagatcaaac | tgcaaggcgg | 420 |
| caacgaggct | gggggagggg | cgcccgccat | tgcccaggct | tgcttaggta | aacaaagcag | 480 |
| ccgggaagct | cgaactgggt | ggagcccacc | acagctcaag | gaggcctgcc | tgcctctgta | 540 |
| ggctccacct | ctgggggcag | ggcacagaca | aacaaaaaga | cagcagtaac | ctctgcagac | 600 |
| ttaagtgtcc | ctgtctgaca | gctttgaaga | gagcagtggt | tctcccagca | cgcagctgga | 660 |
| gatctgagaa | cgggcagaca | gactgcctcc | tcaagtgggt | ccctgactcc | tgaccccga | 720 |
| gcagcctaac | tgggaggcac | cccccagcag | gggcacactg | acacctcaca | cggcagggta | 780 |
| ttccaacaga | cctgcagctg | agggtcctgt | ctgttagaag | gaaaactaac | aaccagaaag | 840 |
| gacatctaca | ccgaaaaccc | atctgtacat | caccatcatc | aaagaccaaa | agtagataaa | 900 |
| accacaaaga | tggggaaaaa | acagaacaga | aaaactggaa | actctaaaac | gcagagcgcc | 960 |
| tctcctcctc | caaaggaacg | cagttcctca | ccagcaacgg | aacaaagctg | atggagaat | 1020 |
| gattttgacg | agctgagaga | agaaggcttc | agacgatcaa | attactctga | gctacgggag | 1080 |
| gacattcaaa | ccaaaggcaa | agaagttgaa | aactttgaaa | aaatttaga | gaatgtata | 1140 |
| actagaataa | ccaatacaga | gaagtgctta | aaggagctga | tggagctgaa | aaccaaggct | 1200 |
| cgagaactac | gtgaagaatg | cagaagcctc | aggagccgat | gcgatcaact | ggaagaaagg | 1260 |
| gtatcagcaa | tggaagatga | aatgaatgaa | atgaagcgag | aagggaagtt | tagagaaaaa | 1320 |
| agaataaaaa | gaaatgagca | aagcctccaa | gaaatatggg | actatgtgaa | aagaccaaat | 1380 |
| ctacgtctga | ttggtgtacc | tgaaagtgat | gtggagaatg | gaaccaagtt | ggaaaacact | 1440 |
| ctgcaggata | ttatccagga | gaacttcccc | aatctagcaa | ggcaggccaa | cgttcagatt | 1500 |
| caggaaatac | agagaacgcc | acaaagatac | tcctcgagaa | gagcaactcc | aagacacata | 1560 |
| attgtcagat | tcaccaaagt | tgaaatgaag | gaaaaaatgt | taagggcagc | cagagagaaa | 1620 |
| ggtcgggtta | ccctcaaagg | aaagcccatc | agactaacag | tggatctctc | ggcagaaacc | 1680 |
| ctacaagcca | gaagagagtg | ggggccaata | ttcaacattc | ttaaagaaaa | gaattttcaa | 1740 |
| cccagaattt | catatccagc | caaactaagc | ttcataagtg | aaggagaaat | aaaatacttt | 1800 |
| atagacaagc | aaatgttgag | agattttgtc | accaccaggc | ctgccctaaa | agagctcctg | 1860 |
| aaggaagcgc | taaacatgga | aaggaacaac | cggtaccagc | cgctgcaaaa | tcatgccaaa | 1920 |
| atgtaaagac | catcgagact | aggaagaaac | tgcatcaact | aatgagcaaa | atcaccagct | 1980 |

```
aacatcataa tgacaggatc aaattcacac ataacaatat taactttaaa tataaatgga    2040
ctaaattctg caattaaaag acacagactg gcaagttgga taaagagtca agacccatca    2100
gtgtgctgta ttcaggaaac ccatctcacg tgcagagaca cacataggct caaaataaaa    2160
ggatggagga agatctacca agccaatgga aaacaaaaaa aggcagggt tgcaatccta    2220 gtctctgata aaacagactt taaaccaaca aagatcaaaa gagacaaaga aggccattac    2280
ataatggtaa agggatcaat tcaacaagag gagctaacta tcctaaatat ttatgcaccc    2340
aatacaggag cacccagatt cataaagcaa gtcctcagtg acctacaaag agacttagac    2400
tcccacacat taataatggg agactttaac accccactgt caacattaga cagatcaacg    2460
agacagaaag tcaacaagga tacccaggaa ttgaactcag ctctgcacca agcagaccta    2520
atagacatct acagaactct ccaccccaaa tcaacagaat atacctttt ttcagcacca    2580 caccacacct attccaaaat tgaccacata gttggaagta aagctctcct cagcaaatgt    2640
aaaagaacag aaattataac aaactatctc tcagaccaca gtgcaatcaa actagaactc    2700
aggattaaga atctcactca aagccgctca actacatgga aactgaacaa cctgctcctg    2760
aatgactact gggtacataa cgaaatgaag gcagaaataa agatgttctt tgaaaccaac    2820
gagaacaaag acaccacata ccagaatctc tgggacgcat tcaaagcagt gtgtagaggg    2880
aaatttatag cactaaatgc ctacaagaga aagcaggaaa gatccaaaat tgacaccta    2940 acatcacaat taaaagaact agaaaagcaa gagcaaacac attcaaaagc tagcagaagg    3000
caagaaataa ctaaaatcag agcagaactg aaggaaatag agacacaaaa aacccttcaa    3060
aaaatcaatg aatccaggag ctggtttttt gaaaggatca acaaaattga tagaccgcta    3120
gcaagactaa taagaaaaa aagagagaag aatcaaatag acacaataaa aaatgataaa    3180
ggggatatca ccaccgatcc cacagaaata caaactacca tcagagaata ctacaaacac    3240
ctctacgcaa ataaactaga aaatctagaa gaatggata cattcctcga cacatacact    3300
ctcccaagac taaaccagga agaagttgaa tctctgaata gaccaataac aggctctgaa    3360
attgtggcaa taatcaatag tttaccaacc aaaaagagtc caggaccaga tggattcaca    3420
gccgaattct accagaggta catggaggaa ctggtaccat tccttctgaa actattccaa    3480
tcaatagaaa aagagggaat cctccctaac tcatttatg aggccagcat cattctgata    3540
ccaaagccgg gcagagacac aaccaaaaaa gagaatttta gaccaatatc cttgatgaac    3600
attgatgcaa aaatcctcaa taaaatactg gcaaaccgaa tccagcagca catcaaaaag    3660
cttatccacc atgatcaagt gggcttcatc cctgggatgc aaggctggtt caatatacgc    3720
aaatcaataa atgtaatcca gcatataaac agagccaaag acaaaaacca catgattatc    3780
tcaatagatg cagaaaaagc cttttgacaaa attcaacaac ccttcatgct aaaaactctc    3840
aataaattag gtattgatgg gacgtatttc aaaataataa gagctatcta tgacaaaccc    3900
acagccaata tcatactgaa tgggcaaaaa ctggaagcat tccctttgaa accggcaca    3960 agacagggat gccctctctc accgctccta ttcaacatag tgttggaagt tctggccagg    4020
gcaatcaggc aggagaagga aataaagggt attcaattag gaaaagagga agtcaaattg    4080
tccctgtttg cagacgacat gattgtatat ctagaaaacc ccatcgtctc agcccaaaat    4140
ctccttaagc tgataagcaa cttcagcaaa gtctcaggat acaaaatcaa tgtacaaaaa    4200
tcacaagcat tcttatacac caacaacaga caaacagaga gccaaatcat gggtgaactc    4260
ccattcgtaa ttgcttcaaa gagaataaaa tacctaggaa tccaacttac aagggatgtg    4320
aaggacctct tcaaggagaa ctacaaacca ctgctcaagg aaataaaaga ggacacaaac    4380
```

-continued

```
aaatggaaga acattccatg ctcatgggta ggaagaatca atatcgtgaa aatggccata    4440
ctgcccaagg taatttacag attcaatgcc atccccatca agctaccaat gactttcttc    4500
acagaattgg aaaaaactac tttaaagttc atatggaacc aaaaaagagc ccgcattgcc    4560
aagtcaatcc taagccaaaa gaacaaagct ggaggcatca cactacctga cttcaaacta    4620
tactacaagg ctacagtaac caaaacagca tggtactggt accaaaacag agatatagat    4680
caatggaaca gaacagagcc ctcagaaata atgccgcata tctacaacta tctgatcttt    4740
gacaaacctg agaaaaacaa gcaatgggga aaggattccc tatttaataa atggtgctgg    4800
gaaaactggc tagccatatg tagaaagctg aaactggatc ccttccttac accttataca    4860
aaaatcaatt caagatggat taaagattta acgttaaac ctaaaaccat aaaaaccta     4920 gaagaaaacc taggcattac cattcaggac ataggcgtgg gcaaggactt catgtccaaa    4980
acaccaaaag caatggcaac aaaagacaaa attgacaaat gggatctaat taaactaaag    5040
agcttctgca cagcaaaaga aactaccatc agagtgaaca ggcaacctac aacatgggag    5100
aaaattttcg caacctactc atctgacaaa gggctaatat ccagaatcta caatgaactt    5160
aaacaaattt acaagaaaaa aacaaacaac cccatcaaaa agtgggcgaa ggacatgaac    5220
agacacttct caaaagaaga catttatgca gccaaaaaac acatgaagaa atgctcatca    5280
tcactggcca tcagagaaat gcaaatcaaa accactatga gatatcatct cacaccagtt    5340
agaatggcaa tcattaaaaa gtcaggaaac aacaggtgct ggagaggatg cggagaaata    5400
ggaacacttt tacactgttg gtgggactgt aaactagttc aaccattgtg gaagtcagtg    5460
tggcgattcc tcagggatct agaactagaa ataccatttg acccagccat cccattactg    5520
ggtatatacc caaatgagta taatcatgc tgctataaag acacatgcac acgtatgttt    5580
attgcggcac tattcacaat agcaaagact tggaaccaac ccaaatgtcc aacaatgata    5640
gactggatta agaaaatgtg gcacatatac accatggaat actatgcagc cataaaaaat    5700
gatgagttca tatcctttgt agggacatgg atgaaattgg aaaccatcat tctcagtaaa    5760
ctatcgcaag aacaaaaaac caaacaccgc atattctcac tcataggtgg gaattgaaca    5820
atgagatcac atggacacag gaagggggaat atcacactct ggggactgtg gtggggtcgg    5880
gggagggggg agggatagca ttgggagata tacctaatgc tagatgacac attagtgggt    5940
gcagcgcacc agcatggcac atgtatacat atgtaactaa cctgcacaat gtgcacatgt    6000
accctaaaac ttagagtata ataaaaaaaa aaaaaaaaaa aaaaaaaaaa aaaaaaaa      6059
```

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cacccacaac gtgcccattt atgag                                           25

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 3
tttgcggtgg acgatggaag g                                              21

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Cys Asp Glu Phe Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Cys Asp His Ile Lys
1               5
```